US008344006B2

(12) United States Patent
Drager et al.

(10) Patent No.: US 8,344,006 B2
(45) Date of Patent: Jan. 1, 2013

(54) LIQUID FORMULATIONS OF BENDAMUSTINE

(75) Inventors: Anthony S. Drager, Thorndale, PA (US); Rachel Y. Labell, Coatesville, PA (US); Piyush R. Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/362,430

(22) Filed: Jan. 31, 2012

(65) Prior Publication Data

US 2012/0129904 A1     May 24, 2012

Related U.S. Application Data

(63) Continuation of application No. 13/048,325, filed on Mar. 15, 2011, which is a continuation of application No. PCT/US2009/058023, filed on Sep. 23, 2009.

(60) Provisional application No. 61/100,074, filed on Sep. 25, 2008.

(51) Int. Cl.
*A61K 31/41* (2006.01)
*A61K 31/195* (2006.01)

(52) U.S. Cl. ......... 514/359; 514/563; 514/724; 514/715

(58) Field of Classification Search .................. 514/359, 514/715, 724, 563
See application file for complete search history.

(56) References Cited

U.S. PATENT DOCUMENTS

| | | | |
|---|---|---|---|
| 4,670,262 A | 6/1987 | Battelli et al. | |
| 5,162,115 A | 11/1992 | Pietronigro | |
| 5,204,335 A | 4/1993 | Sauerbier et al. | |
| 5,227,373 A | 7/1993 | Alexander et al. | |
| 5,750,131 A | 5/1998 | Wichert et al. | |
| 5,770,230 A | 6/1998 | Teagarden et al. | |
| 5,776,456 A | 7/1998 | Anderson et al. | |
| 5,955,504 A | 9/1999 | Wechter et al. | |
| 5,972,912 A | 10/1999 | Marek et al. | |
| 6,034,256 A | 3/2000 | Carter et al. | |
| 6,077,850 A | 6/2000 | Carter et al. | |
| 6,090,365 A | 7/2000 | Kaminski et al. | |
| 6,271,253 B1 | 8/2001 | Carter et al. | |
| 6,380,210 B1 | 4/2002 | Desimone et al. | |
| 6,492,390 B2 | 12/2002 | Carter et al. | |
| 6,545,034 B1 | 4/2003 | Carson et al. | |
| 6,569,402 B1 | 5/2003 | Cheesman et al. | |
| 6,573,292 B1 | 6/2003 | Nardella | |
| 6,613,927 B1 | 9/2003 | Kwok | |
| 2002/0102215 A1 | 8/2002 | Klaveness et al. | |
| 2003/0232874 A1 | 12/2003 | Nardella | |
| 2004/0053972 A1 | 3/2004 | Nara | |
| 2004/0058956 A1 | 3/2004 | Akiyama et al. | |
| 2004/0072889 A1 | 4/2004 | Masjerrer | |
| 2004/0096436 A1 | 5/2004 | Carson et al. | |
| 2004/0152672 A1 | 8/2004 | Carson et al. | |
| 2004/0247600 A1 | 12/2004 | Leoni | |
| 2005/0020615 A1 | 1/2005 | Rubino | |
| 2005/0060028 A1 | 3/2005 | Horres et al. | |
| 2005/0176678 A1 | 8/2005 | Horres et al. | |
| 2006/0051412 A1 | 3/2006 | Petereit et al. | |
| 2006/0159713 A1 | 7/2006 | Brittain et al. | |
| 2009/0264488 A1* | 10/2009 | Cooper et al. ............... 514/394 | |
| 2011/0190363 A1 | 8/2011 | Drager et al. | |

FOREIGN PATENT DOCUMENTS

| | | |
|---|---|---|
| DE | 80967 | 6/1970 |
| DE | 159289 | 3/1983 |
| DE | 159877 | 4/1983 |
| DE | 293808 | 9/1991 |
| DE | 10016077 | 12/2001 |
| DE | 10306724 | 9/2003 |
| DE | 10304403 | 8/2004 |
| EP | 0656211 | 6/1995 |
| EP | 1354952 | 10/2003 |
| EP | 1444989 | 8/2004 |
| WO | WO 96/28148 | 9/1996 |
| WO | WO 03/066027 | 8/2003 |
| WO | WO 03/081238 | 10/2003 |
| WO | WO 03/086470 | 10/2003 |
| WO | WO 03/094990 | 11/2003 |
| WO | WO 2006/076620 | 7/2006 |
| WO | WO 2009/120386 | 10/2009 |
| WO | WO 2010/036702 | 4/2010 |

OTHER PUBLICATIONS

Spiegel et al., Journal of Pharmaceutical Sciences, 1963, vol. 52, pp. 917-927.*
Aivado et al., "Bendamustine in the treatment of chronic lymphocytic leukemia: Results and future perspectives", Seminars in Oncology, Aug. 2002, 29(4), 19-22, Suppl. 13.
Barman Balfour et al., "Bendamustine", Drugs, 2001, 61(5), 631-638, Auckland, New mckimZealand.
Bremer, Karl, "High rates of long-lasting remissions after 5-day bendamustine chemotherapy cycles in pre-treated low-grade non-hodgkin 's-lymphomas", Journal of Cancer Research and Clinical Oncology, 2002, 128(11), 603-609.
Chow et al., "Anti-CD20 antibody (IDEC-C2B8, rituximab) enhances efficacy of cytotoxic drugs on neoplastic lymphocytes in vitro: role of cytokines complement, and caspases", Haematologica, Jan. 2002, 87(1), 33-43.
Chow et al., "In AML Cell Lines Ara-C Combined with Purine Analogues is Able to Exert Synergistic as Well as Antagonistic Effects on Proliferation, Apoptosis and Disruption of Mitochondrial Membrane Potential", Leukemia & Lymphoma, 2003, 44(1), 165-173.
Chow et al., "In vitro induction of apoptosis of neoplastic cells in low-grade non-Hodkin 's lymphomas by combinations of established cytotoxic drugs with bendamustine", Haematologica, May 2001, 86(5), 485-493.
Chow et al., "Synergistic effects of chemotherapeutic drugs in lymphoma cells are associated with down-regulation of inhibitor of apoptosis proteins (IAPs), prostate-apoptosis-response-gene 4(Par-4), death-associated protein (Dazz) and with enforced caspase activation", Biochemical Pharmacology, Jan. 2003, 66(5), 711-724.
Diehl et al., "Bendamustine in the Treatment of Hematologic Malignancies", Semin. Oncol., Aug. 2002, 29(4), 1-3, Suppl. 13, Saundes, Philadelphia, PA.

(Continued)

*Primary Examiner* — Sreeni Padmanabhan
*Assistant Examiner* — Shobha Kantammeni
(74) *Attorney, Agent, or Firm* — Woodcock Washburn LLP

(57) ABSTRACT

Stable liquid formulations of bendamustine, and pharmaceutically acceptable salts thereof, and polar aprotic solvents, are described.

10 Claims, 4 Drawing Sheets

OTHER PUBLICATIONS

Fichtner et al., "Antineoplastic activity and toxicity of some alkylating cytostatics (cyclophosphamide, CCNU, cytostasan) encapsulated in liposomes in different murine tumor models", Journal of Microencapsulation, Jan. 1986, 3(2), 77-87.

Gandhi, Varsha, "Metabolism and mechanisms of action of bendamustine: Rationales for combination therapies", Seminars in Oncology, Aug. 2002, 29(4), 4-11, Suppl. 13.

Gust et al., "Investigations on the Stability of Bendamustin, a Cytostatic Agent of the Nitrogen Mustard Type, I. Synthesis, Isolation, and Characterization of Reference Substances", Monatshefte fur Chemie, 1997, 128(3), 291-299.

Heider et al., "Efficacy and toxicity of bendamustine in patients with relapsed low-grade non-Hodgkin's lymphomas", Anti-Cancer Drugs, 2001, 12(9), 725-729.

International Patent Application No. PCT/US2009/058023: International Search Report dated Feb. 8, 2010, 4 pages.

Kath et al., "Bendamustine monotherapy in advanced and refractory chronic lymphocytic leukemia", Journal of Cancer Research and Clinical Oncology, 2001, 127(1), 48-54.

Koenigsman et al., "Fludarabine and Bendamustine in Refractory and Relapsed Indolent Lymphoma a Multicenter Phase IIII Trial of the East German Society of Hematology and Oncology (OSHO)", Leukemia & Lymphoma, 2004, 45(9), 1821-1827.

Kollmannsberger et al., "Phase II study of bendamustine in patients with relapsed or cisplatin-refractory germ cell cancer", Anti-Cancer Drugs, 2000, 11(17), 535-539.

Konstantinov et al., Cytotoxic efficacy of bendamustine in human leukemia and breast cancer eel/lines, Journal of Cancer Research and Clinical Oncology, 2002, 128(5), 271-278.

Köster et al., "Carboplatin in combination with bendamustine in previously untreated patients with extensive-stage small lung cancer (SCLC)", Clinical Drug Investigation, 2004, 24(10), 611-618.

Leoni et al., "Sdx-105 (Trenda), Active in Non-Hodgkins Lymphoma Cells, Induces the Mitotic Catastrophe Death Pathway", Blood, 104(11), 2004, Abs 4593, p. 232b.

Maas, "Stabilitat von Benamustinhydrochlorid in Infusionslosungen", Pharmazie, 1994, 49(10), 775-777.

McKim et al., "Dimethyl Sulfoxide USP, PhEur in Approved Pharmaceutical Products and Medical Devices," Pharmaceutical Technology, May 2, 2008, 1-7.

Mottu et al., "Organic solvents for pharmaceutical parenterals and embolic liquids: A review of toxicity data," PDA J. Pharma. Sci. & Tech. 54(6) Nov.-Dec. 2000, 456-469.

Niemeyer et al., "SDX-105 (bendamustine) is a clinically active chemotherapeutic agent with a distinct mechanism of action", Proc Annu Meet Am Assoc Cancer Res, Mar. 2004, 45, 1st ed., 2 pages.

Nowak et al., "Upon Drug-Induced Apoptosis in Lymphoma Cells X-linked Inhibitor of Apoptosis (XIAP) Translocates from the Cytosol to the Nucleus", Leukemia & Lymphoma, Jul. 2004, 45(7), 1429-1436.

Ponisch et al., "Bendamustine in the treatment of Multiple Myeloma: Results and future perspectives", Seminars in Oncology, Aug. 2002, 29(4), 23-26, Suppl. 13.

Preiss et al., "Pharmacokinetics of bendamustin (Cytostasan) in patients", Pharmazie, Mar. 1985, 40(11), 782-784.

Ribomustin: Bendamustine Product Monograph, Jan. 2002, 3-58, Ribosepharm GMBH, Munchen, Germany.

Ribomustin: Bendamustine Product Monograph, Mar. 2005, 3-73, Ribosepharm MBH, Munchen, Germany.

Rummel et al., "Bendamustine in the treatment of non-Hodgkin's lymphoma: Results and future perspectives", Seminars in Oncology, Aug. 2002, 29(4), 27-32, Suppl. 13.

Rummel et al., "In Vitro Studies With Bendaustine: Enhanced Activity in Combination With Rituximab", Seminars in Oncology, Aug. 2002, 29(4), 12-14, Suppl. 13.

Scasnar et al., "Radiochemical Assay of Stability of $^{14}$C-Cytostasan Solutions During Preparation and Storage", Journal of Radioanalytical and Nuclear Chemistry, 1998, 121(2), 489-497.

Scasnar et al., "Stability Studies of $^{14}$C-Cytostasan® solutions and its extraction using dicarbolide of cobalt", Phamazie, Mar. 1988, 43, 176-179.

Schmidt-Hieber et al., "A phase II study of bendamustine chemotherapy as second-line treatment in metastatic uveal melanoma", Melanoma Research, 2004, 14(6), 439-442.

Schoffski et al., "Repeated administration of short infusions of Bendamustine: a phase I study in patients with advanced progressive solid tumors", Journal of Cancer Research and Clinical Oncology, 2000, 126(1), 41-47.

Schrijvers et al., "Phase I studies with bendamustine: An update", Seminars in Oncology, 2002, 29(4), 15-18, Suppl. 13.

Strumberg et al., "Bendamustine hydrochloride activity against doxorubicin-resistant human breast carcinoma eel/lines", Anti-Cancer Drugs, 1996, 7(4), 415-421.

Weide et al., "Bendamustine mitoxantrone and rituximab (BMR): A new effective regimen for refractory or relapsed indolent lymphomas", Leukemia & Lymphoma, 2002, 43(2), 327-331.

Weide et al., "Bendamustine/Mitoxantrone/Rituximab (BMR): A Very Effective, Well Tolerated Outpatient Chemoimmunotherapy for Relapsed and Refractory CD20-positive Indolent Malignancies. Final Results of a Pilot Study", Leukemia & Lymphoma, 2004, 45(12), 2445-2449.

Werner et al., "Hydrolyseprodukte des Cancerostaticums Cytostasan (Bendamustin)", Pharmazie, 1987, 42, 272-273.

Zulkowski, et al., "Regression of brain metastases from breast carcinoma after chemotherapy with bendamustine", Journal of Cancer Research and Clinical Oncology, 2002, 128(2), 111-113.

* cited by examiner

LIQUID FORMULATIONS OF BENDAMUSTINE

CROSS REFERENCE TO RELATED APPLICATIONS

This application is a continuation of U.S. application Ser. No. 13/048,325, filed Mar. 15, 2011, which is a continuation of International Application No. PCT/US2009/58023, filed Sep. 23, 2009, which claims the benefit of U.S. Provisional Application No. 61/100,074, filed Sep. 25, 2008, the entireties of which are incorporated by reference herein.

TECHNICAL FIELD OF THE INVENTION

The present invention relates to liquid formulations of bendamustine, and the pharmaceutical salts thereof.

BACKGROUND OF THE INVENTION

Bendamustine, (4-{5-[bis(2-chloroethyl)amino]-1-methyl-2-benzimidazolyl}butyric

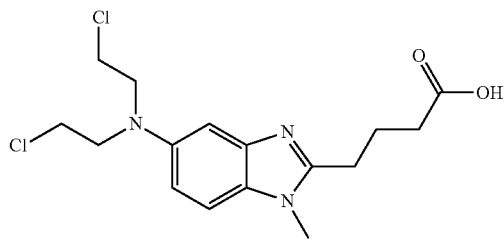

Bendamustine is an atypical structure with a benzimidazole ring, which structure includes an active nitrogen mustard. Bendamustine was initially synthesized in 1963 in the German Democratic Republic and was available from 1971 to 1992 in that location under the name Cytostasan®. Since that time, it has been marketed in Germany under the tradename Ribomustin®. It is currently available for use in the United States under the tradename Treanda® (Cephalon, Inc., Frazer, Pa.). It has been widely used to treat chronic lymphocytic leukemia, Hodgkin's disease, non-Hodgkin's lymphoma, multiple myeloma, and breast cancer.

Like other nitrogen mustards, bendamustine hydrolyzes in aqueous solution, with the major degradant being the primary alcohol HP1 (See U.S. application Ser. No. 11/330,868, the entirety of which is incorporated herein):

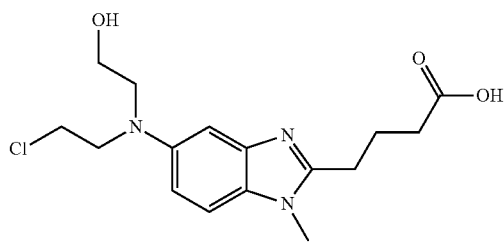 [SMILES: Cn1c(CCCC(=O)O)nc2cc(N(CCCl)CCCl)ccc21]

In light of its instability in aqueous solution, bendamustine is currently supplied as a lyophilized powder for injection. Just prior to its infusion, the medical practitioner reconstitutes the powder with Sterile Water for Injection. Reconstitution should yield a clear, colorless to pale yellow solution and the powder should completely dissolve in about 5 minutes. If particulate matter is observed, the reconstituted product should not be used and should be discarded. The reconstituted product is then transferred to a 0.9% Sodium Chloride Injection infusion bag within 30 minutes of reconstitution. This admixture should be a clear and colorless to slightly yellow solution. If the admixture comprises particulate matter or is discolored, it should be discarded and a fresh sample prepared.

The reconstitution of the bendamustine lyophilized powder is time consuming and cumbersome. Moreover, lyophilization of solids on a commercial scale requires specialized equipment and incurs significant expense. As such, formulations of bendamustine that do not require lyophilization and/or reconstitution are needed.

Solutions of bendamustine hydrochloride in anhydrous propylene glycol, prepared under an inert gas atmosphere, have been reported (GDR Patent 159289). It was reported that analysis of these solutions using thin-layer chromatography, eluting with butanol/acetic acid/water (4:1:5) and detection with Dragendorff reagent and UV (360 nm) did not suggest any decomposition. Curiously, however, commercial development of propylene glycol formulations have heretofore not been reported. Thus, improved liquid formulations of bendamustine are still needed.

SUMMARY OF THE INVENTION

The present invention is directed to liquid pharmaceutical formulations comprising bendamustine, or a pharmaceutically acceptable salt or prodrug thereof, and a polar aprotic solvent. Certain preferred embodiments include liquid pharmaceutical formulations comprising bendamustine, or a pharmaceutically acceptable salt or prodrug thereof, a polar aprotic solvent, and a non-aqueous polar protic solvent. Methods of making and using the formulations of the present invention are also described, as are methods of treating cancer using the claimed formulations.

DETAILED DESCRIPTION OF THE INVENTION

Figure 1:
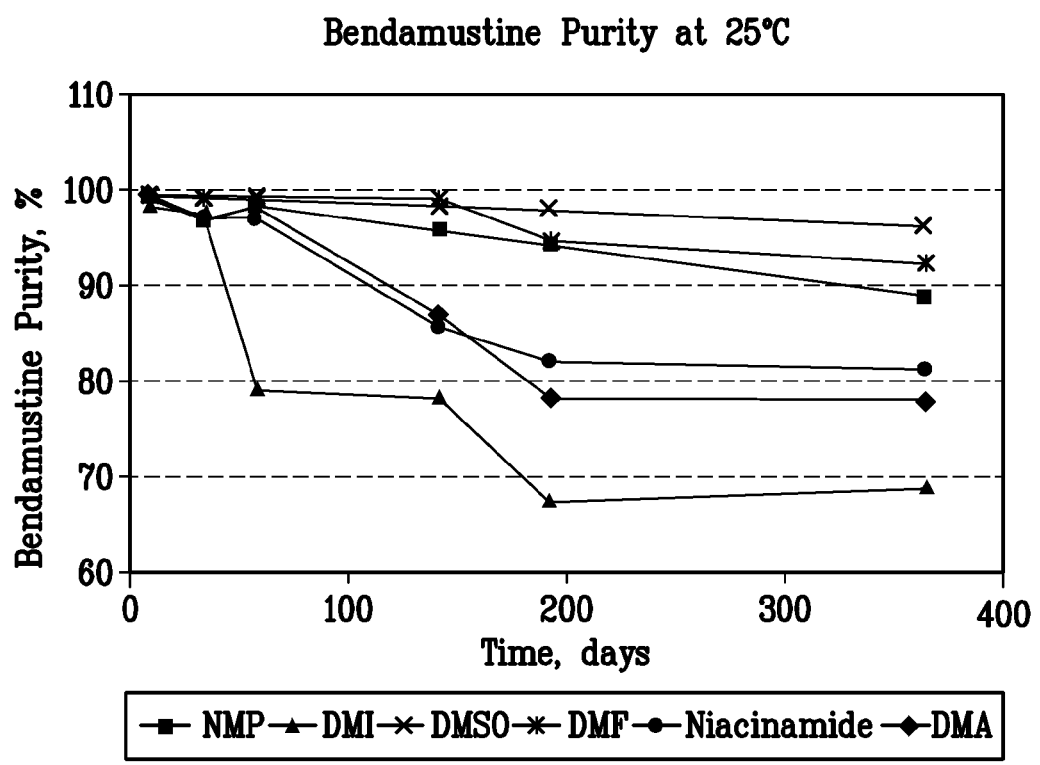
FIG. 1 is a graph of a stability analysis of bendamustine in various solvents at 25° C.

Stable, liquid formulations of bendamustine have been discovered and are reported herein.

Experiments to produce commercially viable propylene glycol preparations have been performed. Unfortunately, the results described in GDR Patent 159289 were not reproducible. Solutions of bendamustine in 99% propylene glycol degraded to non-bendamustine products over a time equivalent to commercial storage. Two of the impurities were identified as propylene glycol esters of bendamustine. As such, a 100% propylene glycol commercial formulation of bendamustine is not feasible for pharmaceutical purposes.

It has been determined that pharmaceutically acceptable liquid formulations of bendamustine, and the pharmaceutically acceptable salts thereof, in particular the hydrochloride salt, can be prepared by combining bendamustine, or the pharmaceutically acceptable salt thereof, with a polar aprotic solvent or mixture of polar aprotic solvents. Polar, aprotic solvents are known in the art and include, for example, 1-methyl-2-pyrrolidone, 1,3-dimethyl-2-imidazolidinone, dimethylacetamide, dimethyl sulfoxide, acetone, tetrahydrofuran, 1,4-dioxane, acetonitrile, dimethyl formamide, propylene carbonate. See also, e.g., Florence Mottu, et al. *Organic solvents for pharmaceutical parenterals and embolic liquids: A review of toxicity data*, PDA J. Pharma. Sci. & Tech. vol 54, no. 6, 456-469 (November-December 2000). Particularly preferred polar aprotic solvents include dimethylacetamide, dimethyl sulfoxide, and mixtures thereof.

Without wishing to be held to any particular theory, it is believed that polar, aprotic solvents are sufficiently non-nucleophilic towards bendamustine such that polar aprotic solvent-bendamustine adducts do not form over the course of typical commercial storage conditions. Typical commercial storage conditions include time periods of, for example, about 30 days, about 90 days, about 180 days, and about 365 days (about 1 month, about 3 months, about 6 months, and about 1 year). Typical commercial storage conditions also include temperatures of about 23° C. (ambient room temperature) and refrigerated temperatures below ambient room temperature, for example, about 5° C. Preferably, the liquid formulations of the present invention are stored at refrigerated temperatures.

It has also been discovered that stable formulations of bendamustine can be obtained by mixing a polar aprotic solvent, or a mixture of polar aprotic solvents, with a nonaqueous polar protic solvent or mixture of nonaqueous polar protic solvents. Pharmaceutically acceptable nonaqueous polar protic solvents are known in the art and include alkyl alcohols, for example, ethanol, ethylene glycol, propylene glycol, butylene glycol, glycerin, polysorbates, for example TWEEN 20, TWEEN 40, and TWEEN 80, and cyclodextrins (such as hydroxypropyl-β-cyclodextrin), polyalkylene glycols, such as polyethylene glycol, polypropylene glycol, and polybutylene glycol, and primary amides such as niacinamide.

Such formulations will typically comprise 90% or less, by volume of the formulation, of the nonaqueous polar protic solvent. In other preferred embodiments, formulations will comprise between about 20% and about 85%, by volume of the formulation, of the nonaqueous polar protic solvent. In still other embodiments, formulations will comprise between about 30% and about 70%, by volume of the formulation, of the nonaqueous polar protic solvent. In most preferred embodiments, formulations will comprise about 80%, about 67% or about 34%, by volume of the formulation, of the nonaqueous polar protic solvent.

Alternatively, formulations of the present invention will comprise 10 moles per liter, or less, of the nonaqueous polar protic solvent. Preferably, formulations of the present invention will comprise between about 4 moles per liter to about 9.5 moles per liter, of the nonaqueous polar protic solvent. In certain embodiments, formulations will comprise about 9.1 moles per liter of the nonaqueous polar protic solvent. In other embodiments, formulations will comprise about 4.6 moles per liter, of the nonaqueous polar protic solvent.

While not wishing to be held to any particular theory, it is believed that while nonaqueous polar protic solvents are of sufficient nucleophilicity to form potentially undesirable polar protic solvent-bendamustine adducts, such adducts will not form during typical commercial storage if the concentration of the polar protic solvent is kept within the scope of the present invention.

Liquid formulations of the present invention are stable over the course of a typical commercial storage period. As used herein, "stable" is defined as no more than about a 10% loss of bendamustine under typical commercial storage conditions. Preferably, formulations of the present inventions will have no more than about a 10% loss of bendamustine, more preferably, no more than about a 5% loss of bendamustine, under typical commercial storage conditions.

Bendamustine converts to non-bendamustine products (i.e., "degrades") upon exposure to certain nucleophiles, for example, water and alkyene glycols such as propylene glycol. Exposure of bendamustine to water can produce "HP1," which is undesirable.

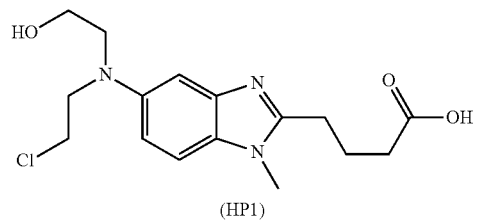

(HP1)

Another undesirable compound that bendamustine can convert to over time is "BM1 dimer"

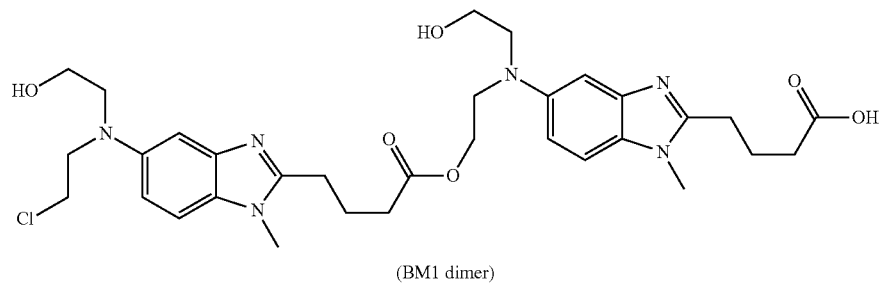 [SMILES: Cn1c(CCCC(=O)O)nc2cc(N(CCO)CCOC(=O)CCCc3nc4cc(N(CCO)CCCl)ccc4n3C)ccc21]

(BM1 dimer)

Still another undesirable compound that bendamustine can convert to over time is "DCE."

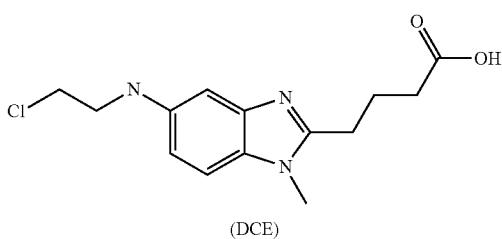 [SMILES: Cn1c(CCCC(=O)O)nc2cc(NCCCl)ccc21]

(DCE)

Upon exposure to an alkylene glycol, for example, propylene glycol, esters of bendamustine can form, e.g., PG-1 and PG-2.

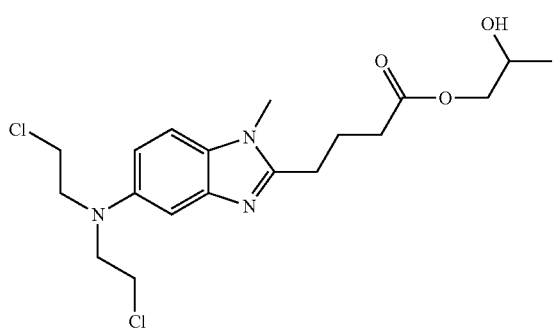

PG-1

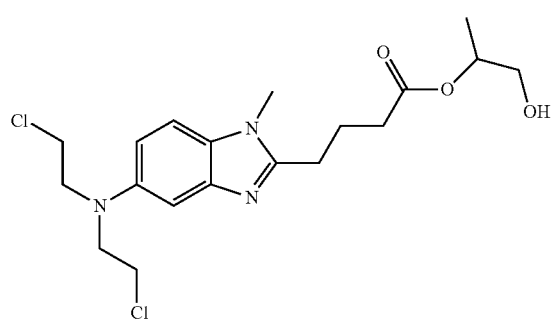

PG-2

In preferred embodiments of the present invention, analysis of formulations of the present invention will exhibit 1.50% or less of DCE, as determined by HPLC analysis, after about 1 year (about 365 days) at about 5° C. More preferably, the formulations will exhibit 1.0% or less of DCE, as determined by HPLC analysis, after about 1 year (about 365 days) at about 5° C. Even more preferably, the formulations will exhibit 0.5% or less of DCE, as determined by HPLC analysis, after about 1 year (about 365 days) at about 5° C. Most preferably, the formulations will exhibit about 0.1% or less of DCE, as determined by HPLC analysis, after about 1 year (about 365 days) at about 5° C.

In other embodiments of the present invention, analysis of the formulations will exhibit about 0.4% or less of HP1, as determined by HPLC analysis, after about 1 year (about 365 days) at about 5° C. Preferably, the formulations will exhibit about 0.10% or less of HP1, as determined by HPLC analysis, after about 1 year (about 365 days) at about 5° C.

In certain other embodiments of the present invention, analysis of the formulations will exhibit about 0.70% or less of BM1 dimer, as determined by HPLC analysis, after about 1 year (about 365 days) at about 5° C. Preferably, the formulations will exhibit about 0.30% or less of dimer, as determined by HPLC analysis, after about 1 year (about 365 days) at about 5° C. In most preferred embodiments, the formulations will exhibit about 0.10% or less of BM1 dimer, as determined by HPLC analysis, after about 1 year (about 365 days) at about 5° C.

In those embodiments of the present invention comprising alkylene glycol as the nonaqueous polar protic solvent, analysis of those formulations will exhibit 1.5% or less of alkylene glycol esters of bendamustine, as determined by HPLC analysis, after about 1 year (about 365 days) at about 5° C. For example, in those embodiments comprising propylene glycol, analysis of those formulations will exhibit 1.5% or less of propylene glycol esters PG-1 and PG-2, as determined by HPLC analysis, after about 1 year (about 365 days) at about 5° C.

Analysis of the liquid formulations of the present invention can be performed using techniques known in the art, including, for example, HPLC, gas chromatography, and NMR. After exposure to typical commercial storage conditions, analysis of the formulations of the present invention will indicate that the formulation contains no less than about 90% of the amount of bendamustine present prior to exposure to the storage conditions. Preferably, analysis will indicate that the formulation contains no less than about 95% of the amount of bendamustine present prior to exposure to the storage conditions.

In preferred embodiments of the present invention, analysis of the formulations of the present invention will indicate that the formulation contains no less than about 90% of the amount of bendamustine present prior to exposure to storage conditions that include temperatures of about 5° C. and time periods of about 30 days (about 1 month) to about 365 days (about 1 year). Preferably, analysis of the formulations of the present invention will indicate that the formulation contains no less than about 90% of the amount of bendamustine present prior to exposure to storage conditions that include temperatures of about 5° C. and time periods of about 30 days (about 1 month), about 90 days (about 3 months), and about 180 days (about 6 months). Preferably, analysis will indicate that the formulation contains no less than about 95% of the amount of bendamustine present prior to exposure to storage conditions that include temperatures of about 5° C. and time periods of about 30 days (about 1 month) to about 365 days (about 1 year). More preferably, analysis will indicate that the formulation contains no less than about 95% of the amount of bendamustine present prior to exposure to storage conditions that include temperatures of about 5° C. and time periods of about 30 days (about 1 month), about 90 days (about 3 months), and about 180 days (about 6 months).

Formulations of the present invention can comprise pharmaceutically useful concentrations of bendamustine, or a pharmaceutically acceptable salt thereof. Useful concentrations include concentrations ranging from about 5 mg/mL to about 200 mg/mL. Preferably, the concentration of bendamustine, or a pharmaceutically acceptable salt thereof, ranges from about 5 mg/mL to about 120 mg/mL. Preferred concentrations include about 5 mg/mL, about 10 mg/mL, about 20 mg/mL, about 30 mg/mL, about 40 mg/mL, about 50 mg/mL, about 60 mg/mL, about 100 mg/mL and about 200 mg/mL of bendamustine, or a pharmaceutically acceptable salt thereof. Greater than 200 mg/ml of bendamustine, or a pharmaceutically acceptable salt thereof, for example, greater than about 300 mg/mL, are also within the scope of the present invention, as are saturated solutions of bendamustine, or a pharmaceutically acceptable salt thereof.

As used herein, the term "about" is defined as ±10%, preferably ±5%,

In addition to comprising a polar aprotic solvent, or mixture of polar aprotic solvents, and optionally, a nonaqueous polar protic solvent, or mixture of solvents, formulations of the present invention may further comprise other pharmaceutically acceptable excipients. Pharmaceutically acceptable excipients are known in the art and include, for example, antioxidants (e.g., tocopherol (Vitamin E), ascorbic acid, methyl paraben, butylhydroxyanisole (BHA), butylhydroxytoluene (BHT), and propyl gallate), surfactants, (e.g., polysorbates (TWEEN 20, TWEEN 40, TWEEN 80)), lipids (e.g., dimyristoylphophatidylcholine (DMPC), Dimyristoylphosphatidylglycerol (DMPG), distearoylphophatidylglycerol (DSPG), fillers (e.g., mannitol), organic acids (e.g., citric acid, lactic acid, benzoic acid), hydrophilic polymers (e.g., polyethylene glycols (PEG 300, PEG 400), complexing agents (e.g., niacinamide, nicotinic acid, creatine, cyclodextrins), and preservatives (e.g., benzyl alcohol).

Also within the scope of the invention are methods of treating diseases, such as, for example, chronic lymphocytic leukemia, Hodgkin's disease, non-Hodgkin's lymphoma, multiple myeloma, or breast cancer, with a pharmaceutical formulation of the present invention. These methods comprise administering to the patient a therapeutically effective amount of a preparation prepared from a pharmaceutical formulation of the present invention. The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

The liquid formulations of bendamustine described herein are intended to be administered via injection, for example, they may be administered subcutaneously, intracutaneously, intravenously, intramuscularly, intra-articularly, intrasynovially, intrasternally, intrathecally, intralesionally, intracranially or via infusion. In a typical preparation, the volume of the liquid formulation of the present invention needed for the required dose can be aseptically withdrawn and transferred to an infusion bag of 0.9% Sodium Chloride (or other pharmaceutically acceptable intravenous solution) for injection. After transfer, the contents of the infusion bag are thoroughly mixed. Administration by intravenous infusion is typically provided over a time period of from about 30 to about 60 minutes. Previously described lyophilized formulations of bendamustine required reconstitution of the lyophilized bendamustine prior to mixture with the acceptable intravenous solution before infusion.

It is envisioned that the pharmaceutical formulations and preparations of the present invention can be administered in combination with one or more anti-neoplastic agents where the anti-neoplastic agent is given prior to, concurrently with, or subsequent to the administration of the formulation or preparation of the present invention. Pharmaceutically acceptable anti-neoplastic agents are known in the art. Preferred anti-neoplastic agents are those disclosed in co-pending U.S. application Ser. No. 11/330,868, filed Jan. 12, 2006, the entirety of which is incorporated herein by reference.

EXAMPLES

Solubility and Stability of Bendamustine Hydrochloride in Polar Aprotic Solvents Equilibrium solubility was determined for solvents including 1-methyl-2-pyrrolidone (NMP), 1,3-dimethyl-2-imidazolidinone (DMI), dimethylacetamide (DMA), dimethyl sulfoxide (DMSO), acetone, tetrahydrofuran (THF), dimethylformamide (DMF), and propylene carbonate (PC). The solubility of bendamustine hydrochloride was also determined for two solutions, 25 mg/mL niacinamide in DMA and 66% DMA/34% propylene glycol (PG). A saturated solution of bendamustine hydrochloride was made in triplicate for each solvent or solution and mixed on a Lab-Quake with gentle mixing and low shear for 3 days at room temperature. A sample of each suspension was put into a microcentrifuge tube and spun at 10,000 rpm for 5 min on an Eppendorf microcentrifuge. The supernatant was removed and put into a clean vial. Each solution was diluted with sample solvent: 50% NMP/50% 0.1% trifluoroacetic acid in water. A reverse phase method for bendamustine hydrochloride was used to determine the concentration of each sample calculated from a standard. Analysis was performed within 18 hours of preparation of the diluted sample. The solubilities are listed in Table I below. Each value is an average of three samples.

TABLE I

| Sample* | % Purity | Assay (mg/mL) |
|---|---|---|
| NMP | 99.1 | 104.0 |
| DMI | 98.5 | 75.8 |
| DMSO | 99.5 | 311.7 |
| DMF | 99.6 | 71.8 |
| 66% DMA/34% PG | 99.5 | 110.1 |
| DMA | 99.4 | 56.2 |
| PC | 98.7 | 7.7 |
| Niacinamide/DMA | 99.2 | 61.3 |

*acetone and THF have no measurable solubility of bendamustine.

Figure 2:
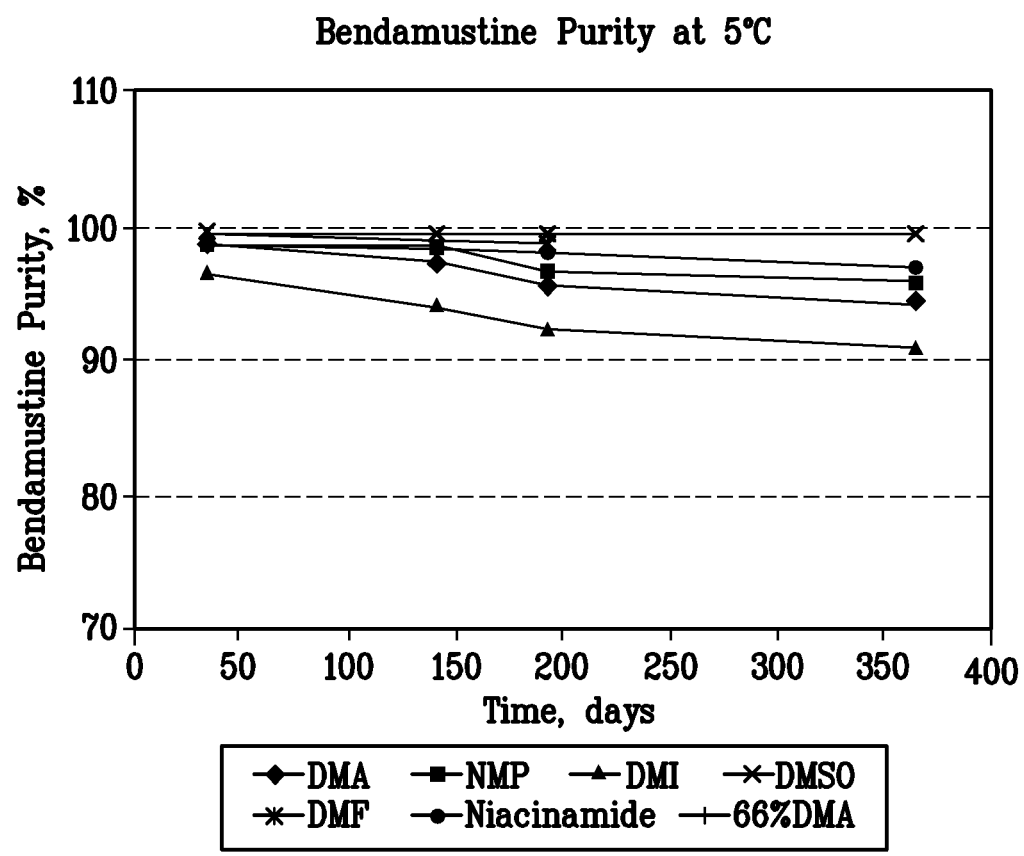
FIG. 2 is a graph of a stability analysis of bendamustine in various solvents at 5° C.

The three replicates were combined and mixed well and then pipetted into amber HPLC vials and placed in stability chambers at 25° C. and 5° C. All the samples were clear and colorless except for the DMI sample which was clear and yellow. The 25° C. stability leveled out from about 180 days (about 6 months) to about 365 days (about 12 months, about 1 year). At 5° C., all solutions had a purity greater than 90%. The analysis of stability samples can be seen in the graphs of FIGS. 1 and 2.

TABLE II

Impurity profile of certain liquid formulations of Bendamustine HCl after storage at 5° C. for about 12 months

| Formulation | DCE (Area %) | HP1 (Area %) | BM1 dimer (Area %) | PG-1 (Area %) | PG-2 (Area %) |
|---|---|---|---|---|---|
| Niacinamide/DMA | 1.40 | 0.08 | 0.06 | ND | ND |
| DMA | 1.10 | 0.08 | 0.05 | ND | ND |
| 66% DMA/34% PG | 0.12 | 0.08 | 0.06 | 1.09 | 0.27 |
| DMF | 0.07 | 0.11 | 0.07 | ND | ND |
| NMP | 0.90 | 0.10 | ND | ND | ND |
| DMSO | 0.04 | 0.38 | 0.70 | ND | ND |

ND = not detected

Analysis conducted using reverse phase HPLC with 50% NMP/50% 0.1% trifluoroacetic acid in water as the running solvent.

Figure 3:
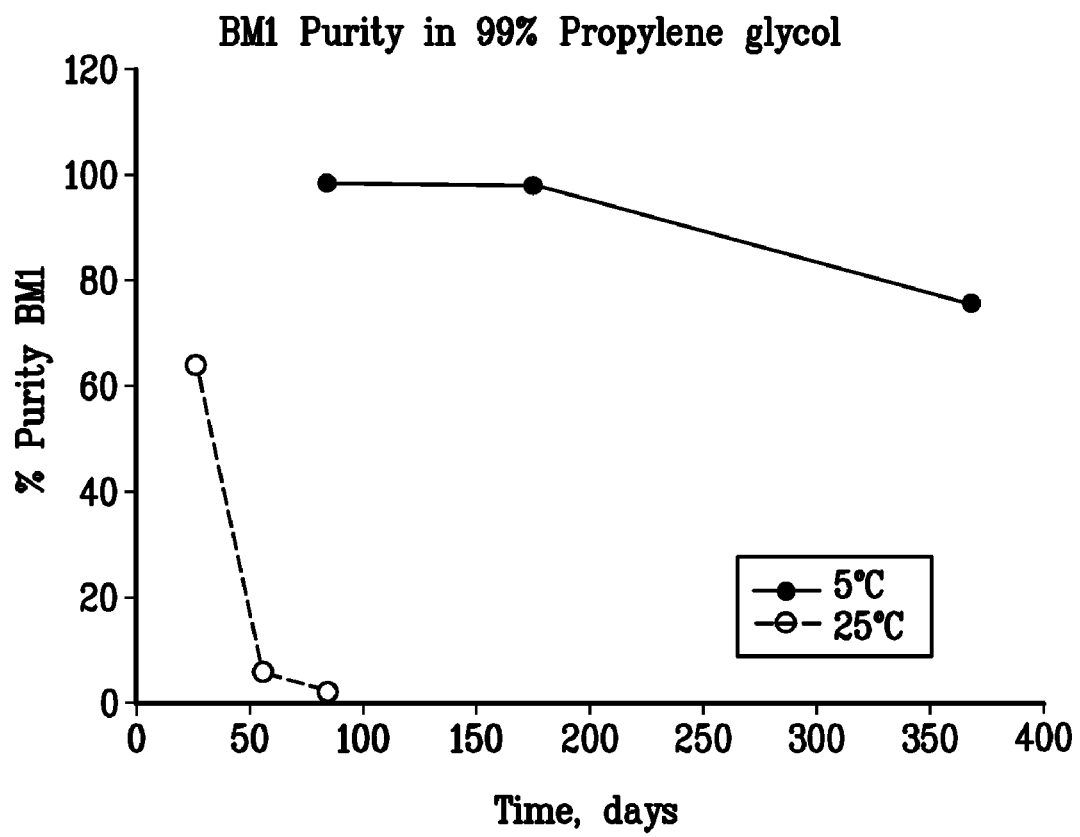
FIG. 3 is a graph of bendamustine purity, over time, in 99% propylene glycol, at 5° C. and at 25° C.

As can be seen in FIG. 3, bendamustine (BM1) in 99% propylene glycol degrades significantly when stored at 25° C. for less than 100 days. After storage at 5° C. for about 365 days, the purity of the bendamustine is about 80% or less.

Pharmacokinetic Study of Formulations in Monkey 4 fasted (18 to 23 hr), drug-naive male cynomolgus monkeys consecutively received single 3-mg/kg bolus intravenous doses of bendamustine hydrochloride prepared from 3 different formulations. The formulations evaluated in the study included:

1) TREANDA (lyophilized mixture of bendamustine hydrochloride and mannitol; 25 mg (bendamustine hydrochloride) vials; 2) a 66% dimethylacetamide (DMA)/34% propylene glycol (PG) (w/w) solution (90 mg (bendamustine hydrochloride)/mL stock); and 3) a 100% DMA solution (45 mg (bendamustine hydrochloride)/mL stock). The lyophilized powder and stock solutions of bendamustine hydrochloride were constituted or diluted with 0.9% saline, as appropriate, to give solutions of 3 mg bendamustine hydrochloride/ml, just prior to dose administration. The resulting solutions were administered as a bolus via a saphenous vein at a fixed volume of 1.0 mL/kg. There was at least a 7-day washout period separating successive doses. During all 3 phases of dosing, blood samples for pharmacokinetic profiling of bendamustine and its 2 active circulating metabolites, γ-hydroxybendamustine (M3) and N-des-methylbendamustine (M4), were collected via a femoral vein immediately prior to dosing and at preselected timepoints through 12 hr postdose. Concentrations of bendamustine, M3 and M4 in plasma samples were determined using a validated high-performance liquid chromatography method with tandem mass spectrometric detection (LC-MS/MS) as follows. Bendamustine and the M3 and M4 metabolites are extracted from plasma by protein precipitation using acetonitrile. After the extraction, the aliquoted sample is acidified with 1% formic acid and bendamustine with an added carbon in the carboxylic acid chain is added as an internal standard. The samples are evaporated to dryness and the residue is reconstituted with an acetonitrile/water/formic acid/ammonium formate mixture. The sample is injected into an HPLC system with LC/MS/MS detection using a Phenomenex Synergi Max-RP column with an acetonitrile/water/formic acid/ammonium formate mobile phase. Pharmacokinetic analyses were performed using noncompartmental methods.

Figure 4:
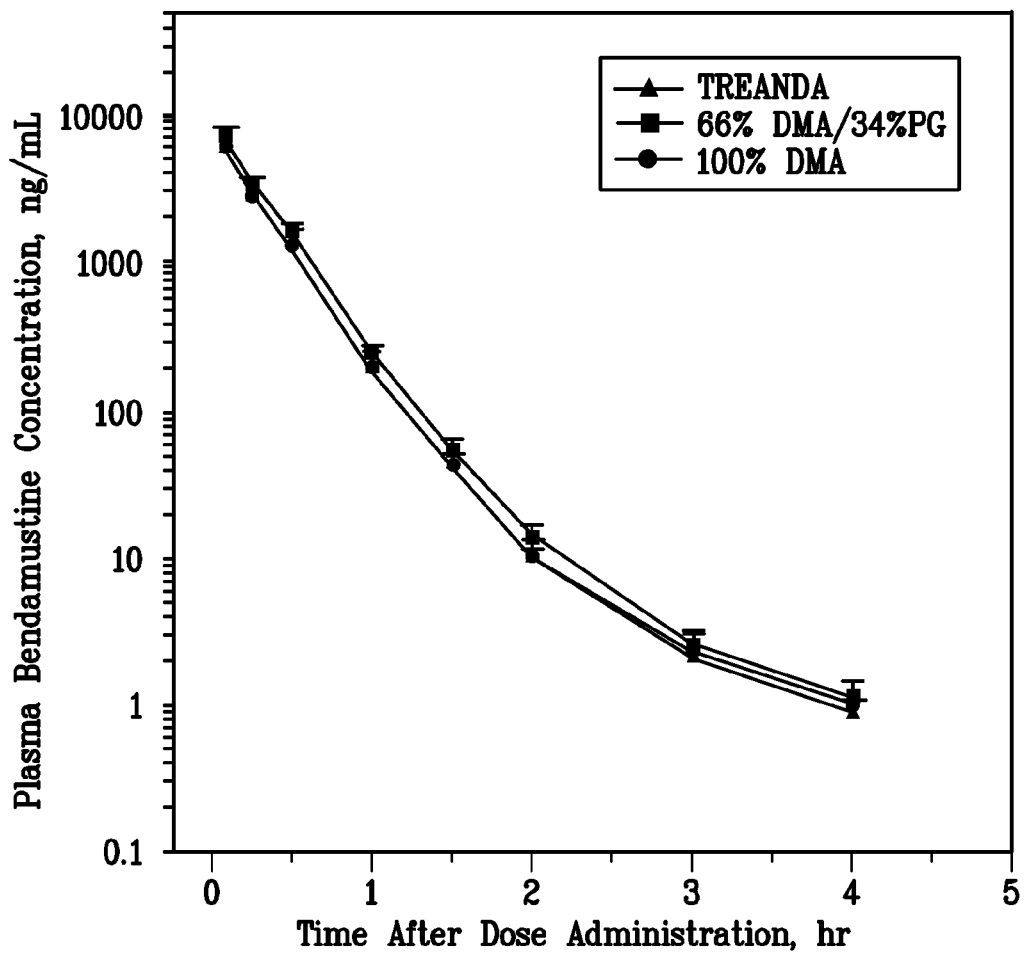
FIG. 4 shows the mean+standard deviation concentration-versus-time profiles of bendamustine in male Cynomolgus monkeys (N=4) administered single 3 mg/kg bolus intravenous doses of bendamustine hydrochloride in 3 different formulations.

After single bolus intravenous doses of bendamustine hydrochloride to male cynomolgus monkeys, the shapes of the mean plasma concentration-versus-time profiles of bendamustine were similar in each of the 3 formulations (See FIG. 4). In all cases, the highest observed plasma levels of bendamustine were achieved at 0.083 hr postdose (ie, the first sampling time after dose administration) and subsequent removal of the compound from plasma occurred in a biphasic manner that was characterized by an initial rapid distribution phase and a somewhat slower terminal phase of drug elimination. The harmonic mean $t_{1/2}$ of the terminal phase was approximately 0.6 hr for each formulation (See Table III).

In addition to the similarities in the shapes of the mean plasma concentration-versus-time profiles, the 3 formulations were also similar with respect to bendamustine systemic exposure (i.e., $C_{max}$ and AUC). Specifically, the respective mean values of $C_{max}$ and $AUC_{0-\infty}$ for bendamustine were 6037 ng/mL and 2314 ng·hr/mL for the TREANDA formulation, 7380 ng/mL and 2854 ng·hr/mL for the 66% DMA/ 34% PG formulation and 6209 ng/mL and 2372 ng·hr/mL for the 100% DMA formulation. Plasma clearance (CL) and volume of distribution ($V_z$ and $V_{ss}$) for bendamustine were also comparable between each of the 3 formulations (See Table III). In Table III, $t_{max}$, hr is given as Median [range], $t_{1/2}$, hr is given as the Harmonic Mean, $\lambda_z$, $hr^{-1}$ is the slope of line in elimination phase used to calculate half-life, and $MRT_{0-\infty}$ is the mean residence time.

In summary, the pharmacokinetic profiles of bendamustine, M3 and M4 for the 2 liquid formulations of bendamustine hydrochloride were qualitatively and quantitatively similar to those obtained for the TREANDA formulation after single bolus intravenous doses to monkeys.

Table III shows the mean+/−Standard Deviation pharmacokinetic parameters of bendamustine in male Cynomolgus monkeys (N=4) administered single 3 mg/kg bolus intravenous doses of bendamustine hydrochloride in the three different formulations.

TABLE III

| | Formulation | | |
|---|---|---|---|
| Parameter | TREANDA | 66% DMA/ 34% PG | 100% DMA |
| $C_0$, ng/mL | 8664 ± 3841 | 10716 ± 2033 | 8956 ± 1965 |
| $C_{max}$, ng/mL | 6037 ± 2456 | 7380 ± 1170 | 6209 ± 1300 |
| $t_{max}$, hr | 0.083 [0.083 for all] | 0.083 [0.083 for all] | 0.083 [0.083 for all] |
| $AUC_{0-t}$, ng · hr/mL | 2313 ± 800 | 2853 ± 398 | 2371 ± 535 |
| $AUC_{0-\infty}$, ng · hr/mL | 2314 ± 800 | 2854 ± 398 | 2372 ± 535 |
| $\lambda_z$, $hr^{-1}$ | 1.220 ± 0.111 | 1.295 ± 0.108 | 1.092 ± 0.219 |
| $t_{1/2}$, hr | 0.57 | 0.54 | 0.63 |
| CL, L/hr/kg | 1.27 ± 0.40 | 0.96 ± 0.14 | 1.18 ± 0.27 |
| $V_z$, L/kg | 1.04 ± 0.36 | 0.74 ± 0.05 | 1.17 ± 0.44 |
| $V_{ss}$, L/kg | 0.34 ± 0.11 | 0.26 ± 0.05 | 0.30 ± 0.04 |
| $MRT_{0-\infty}$, hr | 0.26 ± 0.02 | 0.27 ± 0.02 | 0.26 ± 0.03 |

In-Use Studies of Formulations

Admixtures in 0.9% sodium chloride (500 mL bag) were prepared at a high dose (360 mg bendamustine hydrochloride) and purity was determined over time at room temperature for up to 8 hours using HPLC, using a Zorbax Bonus-RP column with a gradient from 93% 0.1% trifluoroacetic acid in water (Mobile Phase A)/7% 0.1% trifluoroacetic acid in acetonitrile (Mobile Phase B) to 10% Mobile Phase A/90% Mobile Phase B.

The 66% DMA/34% PG formulation had a concentration of bendamustine hydrochloride of 90 mg/g, so 4 mL was injected into a 500 mL bag of saline, inverted 10 times and sampled at room temperature for 8 hours. After 8 hours the purity was 95.4%. This is within the label requirements for dosing Treanda. This formulation of the present invention could be used for up to 8 hours at room temperature. By way of contrast, reconstituted Treanda can only be stored at room temperature for up to 3 hours.

The 100% DMA formulation had a concentration of 45 mg/g, so 8 mL was injected into a 500 mL bag of saline, inverted 10 times, and sampled at room temperature for 4 hours. After 4 hours the purity was 97.9%. This formulation of the present invention could be used for more than 4 hours at room temperature.

The comparative Treanda admixture purity was 95.0% after 4 hours at 25° C.

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

What is claimed is:

1. A stable, non-aqueous liquid, pharmaceutical formulation comprising from about 5 mg/ml to about 120 mg/mL of bendamustine, or a pharmaceutically acceptable salt thereof, solubilized in about 66% (v/v) of dimethylacetamide and about 34% (v/v) of propylene glycol, wherein said formulation, following dilution with a pharmaceutically acceptable diluent, is suitable for injection into a patient without lyophilization.

2. The formulation of claim 1, comprising about 100 mg/mL of bendamustine, or a pharmaceutically acceptable salt thereof.

3. The formulation of claim 1, wherein the bendamustine is bendamustine hydrochloride.

4. The formulation of claim 1, further comprising at least one pharmaceutically acceptable excipient or diluent.

5. The formulation of claim 1, further comprising an antioxidant, a surfactant, a lipid, a filler, an organic acid, a hydrophilic polymer, a complexing agent, a preservative, or a combination thereof.

6. A method of treating chronic lymphocytic leukemia or non-Hodgkin's lymphoma comprising
   providing a liquid, pharmaceutical formulation of claim 1;
   diluting the liquid pharmaceutical formulation with a pharmaceutically acceptable injectable diluent to form an injectable pharmaceutical preparation;
   administering the injectable pharmaceutical preparation to a patient in need of treatment thereof.

7. The method of claim 6, wherein the liquid pharmaceutical formulation comprises about 100 mg/mL of bendamustine, or a pharmaceutically acceptable salt thereof.

8. The method of claim 6, wherein the pharmaceutically acceptable injectable diluent is 0.9% sodium chloride.

9. The formulation of claim 2, comprising 90 mg/mL of bendamustine hydrochloride.

10. The method of claim 7, comprising 90 mg/mL of bendamustine hydrochloride.

* * * * *